United States Patent
Hubbe

(10) Patent No.: US 6,176,974 B1
(45) Date of Patent: Jan. 23, 2001

(54) METHOD FOR DETERMINING ELECTROKINETIC PROPERTIES OF PAPERMAKING FURNISH

(75) Inventor: Martin Allen Hubbe, Campbell Hall, NY (US)

(73) Assignee: International Paper Company, Purchase, NY (US)

(*) Notice: Under 35 U.S.C. 154(b), the term of this patent shall be extended for 0 days.

(21) Appl. No.: 08/995,668

(22) Filed: Dec. 22, 1997

(51) Int. Cl.[7] .............. D21F 11/00; D21F 13/00; D21H 23/00
(52) U.S. Cl. ................................. 162/158; 162/198
(58) Field of Search .......................... 162/158, 198

(56) References Cited

U.S. PATENT DOCUMENTS

| | | | |
|---|---|---|---|
| 3,654,551 | * | 4/1972 | Flinchbaugh ............... 324/71 CP |
| 4,294,656 | * | 10/1981 | Beck et al. ............... 162/192 |
| 4,507,556 | * | 3/1985 | Brenholdt ............... 250/341 |
| 4,517,285 | * | 5/1985 | Woodward et al. ............... 430/538 |
| 4,535,285 | * | 8/1985 | Evans et al. ............... 324/71.1 |
| 4,687,986 | * | 8/1987 | Eriksson ............... 324/71.1 |
| 4,752,356 | * | 6/1988 | Taggert et al. ............... 162/198 |
| 4,873,489 | * | 10/1989 | Melcher et al. ............... 324/453 |
| 4,891,098 | * | 1/1990 | Renjilian et al. ............... 162/198 |
| 4,961,147 | * | 10/1990 | Moore ............... 324/446 |
| 5,119,029 | * | 6/1992 | Bryant et al. ............... 324/453 |
| 5,202,016 | * | 4/1993 | Church et al. ............... 210/85 |
| 5,220,283 | * | 6/1993 | Dentel ............... 324/453 |
| 5,365,775 | * | 11/1994 | Penniman ............... 73/53.04 |
| 5,373,229 | * | 12/1994 | Penniman ............... 324/71.1 |
| 5,408,185 | * | 4/1995 | Krah ............... 324/453 |
| 5,495,751 | * | 3/1996 | Petzold et al. ............... 73/53.03 |

* cited by examiner

Primary Examiner—Christopher A. Fiorilla
(74) Attorney, Agent, or Firm—Luedeka, Neely & Graham, P.C.

(57) ABSTRACT

A method and apparatus for determining electrokinetic properties of a papermaking furnish includes mixing a sample of furnish in a container with a known amount of a charged additive and then measuring the streaming potential of the resultant ionically modified furnish sample. The amount of charged additive added to the container is increased or decreased as repeated streaming potential measurements are made until a desired streaming potential of the modified furnish sample is obtained. The results, which are expressed as the amount of titrant required to achieve the desired streaming potential in a given volume of furnish, may be used by papermakers to adjust process variables and achieve optimum, stable paper quality and machine runnability.

21 Claims, 3 Drawing Sheets

METHOD FOR DETERMINING ELECTROKINETIC PROPERTIES OF PAPERMAKING FURNISH

TECHNICAL FIELD

The present invention relates generally to control of paper formation properties of papermaking furnish. More particularly, it relates to an apparatus and method for measuring and adjusting the electrokinetic charge of papermaking furnish to aid in achieving optimal, stable paper formation properties and machine runnability.

BACKGROUND

During papermaking operations, an aqueous slurry of cellulosic fibers (furnish or pulp) is produced by subjecting wood to various mechanical and/or chemical processes with the aim of liberating and individualizing fibers from the wood stock. For some grades of pulp, the chemical treatment is geared toward removal of lignin from the fibers. The pulp is often subjected to additional chemical treatments such as bleaching where the fibers are further liberated and decolored to lighten the fibers for production of white paper or board product. Bleaching also tends to reduce fiber strength and viscosity, as the chemicals will attack the cellulose to some degree.

Once a pulp of the desired degree of liberation and whiteness if obtained, it is then diluted in water to make what is known as the furnish. The furnish is then sent to a headbox and released from a wide, slit-like opening known as a "slice" and the jet is deposited onto a continuously moving screen or "wire" (also sometimes referred to as a forming fabric) where the furnish is dewatered. As the papermaking furnish is dewatered, fibers and other particulates become trapped by the forming fabric, forming a paper web which is further processed into the end product. To maintain an acceptable rate of production on a commercial paper or paperboard machine, it is essential that the furnish permit sufficiently rapid drainage of the water from the forming mat of fibers.

The papermaker will often tailor the make-up of the furnish using various additives to produce a paper or board sheet with desired formation properties. Many of these additives are supplied as substantially water-insoluble particulate solids in a finely divided state. Exemplary solid particulate additives include clay, calcium carbonate, titanium dioxide, pigment dyes, rosin, and other materials. To achieve the desired effect, it is essential that these additives be efficiently retained in the web forming on the wire.

The furnish used by most papermakers is composed mainly of cellulosic fibers suspended in water such as groundwood pulp, chemithermomechanical pulp (CTMP), kraft pulp, or sulfite pulp. It is the nature of these pulp varieties to have, at the surfaces of fibers and other suspended particles, a net electrical charge. Charges on the surfaces of solids suspended in papermaking furnish arise for several reasons including (a) dissociation of ionizable groups such as carboxylic acids, sulfonic acids, amines, and hydrous oxides, (b) adsorption of ions from solution, and (c) substitution of atoms having differing valence into the lattices of inorganic crystals.

Charges at the surfaces of suspended particles attract ions of opposite charge (counter-ions), resulting in the formation of an ionic double-layer. Some of the counter-ions in the double layer are present immediately adjacent to the charged surface (Stern layer). Thermal energy causes some of the counter-ions to diffuse away from the surface so that they are present as a diffuse cloud of gradually decreasing density of net charge.

The net electrical charge of suspended particles within the furnish can have a profound effect on retention, drainage during web formation, and paper properties. For example, if a new batch of pulp contains a higher level of dissolved anionic polymers and colloidal anionic material (disco), then a decrease in the percentage of fine material retained during a single pass over the forming fabric (first-pass retention) is generally observed. An inherent difficulty, however, is that the colloidal charge of a papermaking furnish is subject to sudden changes. Sources of such disturbances include variations between different batches of pulp, transitions between different types of species of wood in pulping, the use of mechanical pulps of variable quality and variations in pulp washing efficiency, variations in the ratio between different types of pulp, in the amount of broke, in the concentrations of latex dispersants, carry-over of de-inking chemicals, in the level of hemicellulose and byproducts of oxidative bleaching, in micro-biological activity and in the quality of fresh water. Further disturbances in charge may result from changes in the levels of additives such as dyes, wet-strength additives, dry-strength resins, recycled size-press starch,- biocides, colloidal silica, bentonite, and other colloidally charged additives.

As a further source of colloidal charge disturbances, papermakers must deal with the consequences of intermittent interruptions of parts of the system. For example, when the web of paper breaks it must be rethreaded. Such interruptions have the tendency to move the system away from an optimum balance between the chemical additives having opposite colloidal charges, thereby making it more difficult for papermakers to maintain a uniform product.

Therefore, stability and control of the electrokinetic properties of the papermaking furnish is a necessary requirement for the efficient production of a uniform paper product.

Several approaches to monitoring and controlling the electrokinetic properties of a papermaking furnish have previously been attempted. These approaches include laboratory-based tests where a sample is withdrawn from the furnish or from the whitewater which drains from the furnish during web formation. One such lab-based test involves a process known as micro-electrophoresis, in which a microscope is used to observe the motion of a particle in the size range of about 0.2–500 microns as it migrates under the influence of an imposed electric field. The quotient of the particle velocity and the field strength defines the electrophoretic mobility. When the viscosity of the fluid and the conductivity are known, it is possible to calculate the "zeta potential" from this approach, which is the electrical potential at the plane of shear that divides the counter-ions, which tend to stay with the surface, from those ions which tend to move with aqueous fluid flowing past the surface.

Among the difficulties of micro-electrophoresis as applied to the study and control of papermaking operations is the requirement that the observed particles be much smaller than the diameter of the capillary cell in which the tests are conducted. This size requirement usually precludes direct microelectrophoretic analysis of the kind of cellulose fibers used in papermaking. Accordingly, the conventional approach is to screen the fibrous slurry and test the fine suspended solids remaining in the filtrate, or white-water. The capillaries used in micro-electrophoresis measurements are subject to contamination by the many polymeric and particulate ingredients in paper. Also, the focusing of the microscope tends to be too delicate for continuous operation in the industrial environment of a paper mill. An incorrectly focused micro-electrophoresis apparatus will give misleading data that is not representative of the actual zeta potential.

A further problem with micro-electrophoresis is that the information obtained about the electrophoretic mobility, or zeta potential, is usually not linearly proportional with any process or additive which is under the direct control of the papermakers.

Another approach to monitoring the electrokinetic properties of papermaking furnish is to employ a device that measures "streaming current" of a sample of furnish. A typical streaming current device consists of a polytetrafluoroethylene (PTFE) plunger which is reciprocated within a PTFE cylinder containing the furnish sample. The reciprocating motion causes fluid to move rapidly in the annular space between the plunger and cylinder wall. The motion of the fluid induces a streaming current which is detected by connection of a suitable ammeter to electrodes positioned adjacent the annular space. An alternating signal, which is produced by the reciprocating fluid flow, is rectified and smoothed to produce the streaming current information. The accuracy of the streaming current method, however, depends strongly on levels of materials such as sodium sulfate and potassium chloride which are present in the samples being tested.

Yet another method for measuring the electrokinetic charge of papermaking furnish is known as "streaming potential". This method involves measuring the streaming potential resulting from liquid flow through a mat or plug of fibers and other particles collected on a screen. The streaming potential is determined from the change in electrical potential measured between electrodes located on either side of the fiber pad relative to a reference measurement or measurements at a relative pressure across the pad which is different from the first value. Usually, the reference data are obtained at a small or zero pressure difference across the mat or in the absence of a mat.

Streaming potential measurements can be used to gain information about the zeta potential at the surface of the actual fibers. The measurements are repeated often enough to give the papermaker a good idea of how the zeta potential varies as a function of time. However, the accuracy of the absolute magnitudes of the zeta potential is generally considered unreliable due to a perception that the results are dependent on the degree of compaction of the fiber mat. Additionally, streaming potential measurement devices do not provide the papermaker with information about colloidal charge.

Therefore, it is an object of the present invention to provide a method and apparatus for determining electrokinetic properties of a papermaking furnish in order to provide reliable formation-related data.

Another object of the present invention is to provide a method and apparatus which enables a papermaker to measure the colloidal charge of a papermaking furnish.

Yet another object of the invention is to provide a method and apparatus of the character described which promotes efficient use of fiber furnish additives such as highly charged cationic polymers.

A further object of the invention is to provide a method and apparatus of the character described which enables achievement of accurate diagnosis of the root causes of variations in production uniformity and product quality.

An additional object of the invention is to provide a method and apparatus of the character described which enables achievement of optimum performance of furnish additives, retention of fine materials, drainage rates, and uniformity of formation.

Still another object of the invention is to provide a method and apparatus for determining formation-related properties of a furnish to enable control of the web formation by necessary adjustment in the furnish composition.

Yet another object of the invention is to provide a method and apparatus which enables control of the formation properties of papermaking furnish by accurate determination of the electrokinetic charge of the furnish.

SUMMARY

With regard to the foregoing and other objects, the invention provides a new and improved method and apparatus for determining electrokinetic properties of a papermaking furnish. In accordance with its more general aspects, the method comprises mixing a sample of the furnish with a measured amount of a cationic or anionic additive to produce an ionically modified furnish and measuring the streaming potential of the ionically modified furnish. In one application of the method, the amount of the cationic or anionic additive is related to a desired streaming potential and the additive is therefore supplied in an amount necessary to achieve the desired streaming potential through adjustment of the anionic or cationic demand of the furnish sample.

The additive may be supplied or added to the same or a series of fresh furnish samples in increments or in larger or smaller doses with the streaming potential measured between increments or samples. The amounts of additive may be plotted against corresponding streaming potential measurements and the resulting curve or mathematical relationship in the form of an equation fitting the curve used to determine the amount of additive needed to achieve a desired streaming potential in the furnish. The information obtained through use of the method may be used by the papermaker to build an empirical base of data and additive/formation property effects and, ultimately, the additive loading for the furnish to achieve a desired streaming potential and, hence, improved control of the formation properties of the pulp on the machine. The method is adaptable for on-line use to enable rapid, contemporaneous evaluation and adjustment of the ionic properties of the furnish.

The invention further provides an apparatus for determining the cationic or anionic demand of a papermaking furnish. In accordance with its more general aspects, the apparatus comprises a sample chamber equipped to determine the streaming potential of a sample of papermaking furnish contained in the chamber. A first conduit connects the chamber in flow communication with a source of furnish to be sampled and a second conduit connects the chamber in flow communication with a source of a charged additive for addition to the furnish to modify its ionic characteristics. Means are provided for mixing the charged additive and furnish sample to produce an ionically modified furnish sample in the sample chamber. Valves or metering devices are provided in the first and second conduits to supply known amounts of charged additive into the furnish sample. A streaming potential measuring device measures the streaming potential of the ionically modified furnish sample in the sample chamber and produces a streaming potential signal corresponding to the measured streaming potential.

The apparatus may also include a drain conduit connected in flow communication with the chamber for emptying the contents of the chamber when a measurement cycle is completed.

A preferred streaming potential measuring device includes a screen located in the chamber having oppositely facing first and second sides with a mesh size sufficient to inhibit the passage of wood fibers through the screen in a manner similar to that of the forming fabric on the papermaking machine. The device includes means for inducing a flow of the ionically modified furnish sample through the screen so that a layer of fibers is formed adjacent the screen. For example, the layer of fibers can be formed by varying hydrodynamic pressure on one side of the screen relative to the pressure on the other side of the screen such as by a pump or by changing the level of liquid in the chamber with the screen located in a standpipe whose bottom opening is in flow communication with the liquid and whose top opening opens to the air space above the level of the liquid. A voltmeter with electrodes disposed adjacent opposed sides of the screen measures the streaming potential across the plug of fibers as the ionically modified furnish sample is moved through the screen.

A computer may be connected to the apparatus to receive and process a streaming potential signal from the voltmeter and control the overall operation of the apparatus. One of the control functions provided by the computer is to control the amount of the furnish conducted through the chamber and the amount of additive mixed with the furnish by connecting computer output signals to appropriate flow control valves or other suitable metering devices and activation of the computer to generate signals based on conventional sensors such as level sensors and the like.

BRIEF DESCRIPTION OF THE DRAWINGS

The above and other features, aspects and advantages of the present invention will become further known from the following detailed description and appended claims considered in conjunction with the accompanying drawings in which:

DETAILED DESCRIPTION OF A PREFERRED EMBODIMENT

Figure 1:
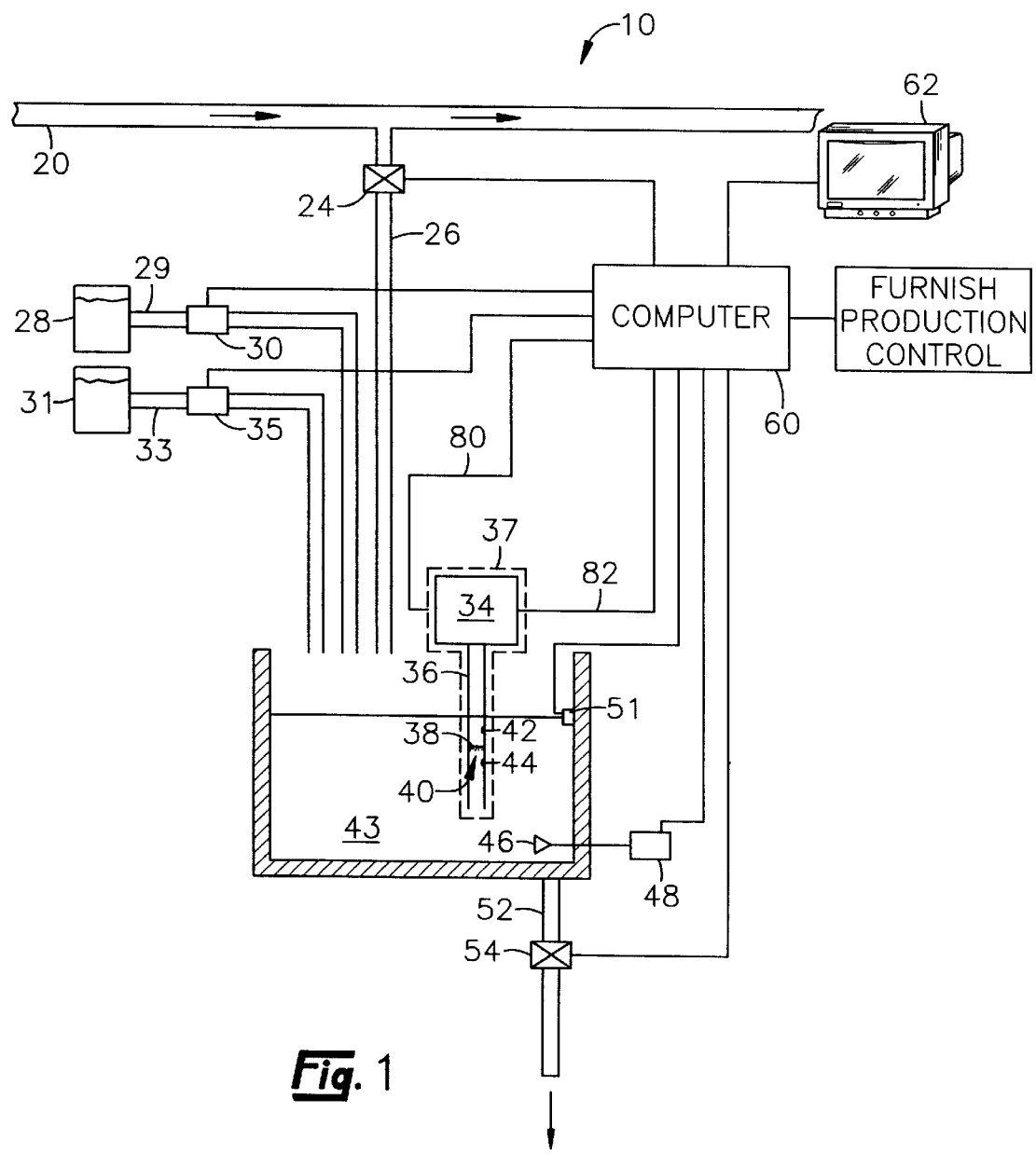
FIG. 1 is a diagrammatical view illustrating features of an apparatus, including separate furnish and titrant supply conduits, for determining the cationic or anionic demand of a papermaking furnish in accordance with a preferred embodiment of the invention.

With reference now to the drawings in which like reference characters designate like or similar parts throughout the several views, FIG. 1 illustrates a system 10 according to the invention for determining the ionic properties of a wood pulp slurry or papermaking furnish in order to enable control of the formation characteristics of a web forming from the slurry or furnish on a paper machine. In general, this is achieved by determining the effect caused by addition of measured amounts of a charged additive to the furnish on its streaming potential and employing this information to determine the amount of additive, if any, to add to the furnish to achieve a desired colloidal charge in the furnish on a papermaking machine. Colloidal charge is determined by the amount of a charged colloidal additive required to titrate a known amount of slurry sample to a desired streaming potential value or endpoint. Although a streaming potential endpoint of zero is preferred, a non-zero streaming potential endpoint may be used instead. For many papermaking applications, the desired colloidal charge of the production furnish is non-zero, but for some applications a colloidal charge of zero may be preferable.

Referring to FIG. 1, a portion of a papermaking furnish which is carried, for example, from a pulp stock tank to a headbox by conduit 20 during papermaking operations is diverted to a sample test chamber 32, or container via sample line 26. A furnish supply valve 24, which is preferably computer controlled by computer 60 but instead may be manually operated, controls the amount of a furnish sample 43 diverted from conduit 20 into the test chamber 32.

A level sensor 51 is positioned in the test chamber 32 to provide a signal to computer 60 to indicate when a desired amount of furnish is present in the test chamber 32. When level sensor 51 indicates that the desired amount of furnish is present, computer 60 closes valve 24. Alternatively, a sample of furnish may be obtained off-line and a measured amount placed in test chamber 32 for testing. In either case, the sample 43 is metered or otherwise measured so that test chamber 32 contains a well-defined quantity of furnish.

It is preferred in the practice of the invention to dilute the furnish sample, if necessary, to a consistency of about 1% before the sample is tested for the effect of various additives. However, the furnish can be used as is, and its consistency may generally range from about 0.01% to about 2%. Of course, any determinations concerning the amount of additive found to be necessary for achieving a desired streaming potential should be adjusted by any dilution of the furnish so that appropriate adjustments in the additives may be made to the undiluted furnish on the machine.

The furnish sample 43 is mixed with a measured amount of a charged additive to determine the effect of the additive on the electrokinetic properties of the furnish relative to a desired streaming potential. In a preferred embodiment, the process for determining the effect of the additive is carried out using a streaming potential device 37. In this manner, results are based on measurements of the electrokinetic effects of the additive at the surface of the actual fibrous material from which paper is made. Measurement results are therefore directly indicative of the colloidal materials adsorbed at the fiber surfaces and may be expressed as the amount of additive required to achieve a given streaming potential per volume of furnish.

In addition to streaming potential measurement device 37, other suitable devices may be used for determining the streaming potential of the ionically modified furnish. For example, the streaming potential measurements of the ionically modified furnish may be taken according to the methods and apparatus described in commonly assigned U.S. Pat. No. 5,936,151 entitled "Method and Apparatus for Measuring an Electrical Property of Papermaking Furnish" filed Dec. 22, 1997, the disclosure of which is incorporated herein by reference.

The results obtained through use of the invention are easy to interpret in terms of control strategies directly usable by operators of paper machines. The measured amounts of additive will generally be directly reflective of the amounts of papermaking additive required to achieve desired formation characteristics for optimum sheet quality, as well as retention, drainage, and uniformity and stability of the paper machine.

From the results, adjustments may be made by the papermaker to effectively compensate for any changes in the level of dissolved and colloidal materials in the furnish, or to respond to changes in the level of broke, web breaks, and other additive flow changes which otherwise would tend to change the conditions of papermaking. The apparatus 10 and practice of the associated method also enables the papermaker to accurately diagnose the root causes of previously unexplained variations in production uniformity and product quality and to optimize chemical dosages to achieve the best performance of furnish additives, retention of fine materials, drainage rates, and uniformity of formation. Monitoring and adjustment of the papermaking furnish in accordance with the invention may either be intermittent or conducted substantially continuously at short intervals.

Since it is the nature of most wood pulp furnishes to have negative (anionic) colloidal charges, the sample 43 is usually mixed with a highly cationic polymer such as poly-diallyldimethylammonium chloride (DADMAC), methylglycolchitosan, or polyamines. However, for furnishes having positive (cationic) colloidal charges, an anionic additive such as colloidal silica, polyvinylsulfate or poly-acrylate is used. It is preferred to provide these materials in an aqueous solution or suspension generally in a concentration of from about 0.1 to 5.0% by weight.

To accommodate testing of both anionic and cationic furnishes, the apparatus 10 preferably includes separate additive sources—an anionic additive reservoir 28 and a cationic additive reservoir 31. Anionic material is released into the test chamber 32 via conduit 29. Metering pump 30 controls and meters the amount of anionic material released. Similarly, cationic material is released from reservoir 31 into the test chamber 32 via line 33 and metered through metering pump 35. While the volumes delivered by pumps 30 and 35 may be determined manually, these pumps are preferably positive displacement pumps capable of delivering liquid flow at a precisely controlled rate. It is preferred to use piston or diaphragm positive displacement pumps, but it is also feasible to use other types of positive displacement pumps such as peristaltic pumps or standard pumps together with a positive displacement flow meter.

Figure 2:
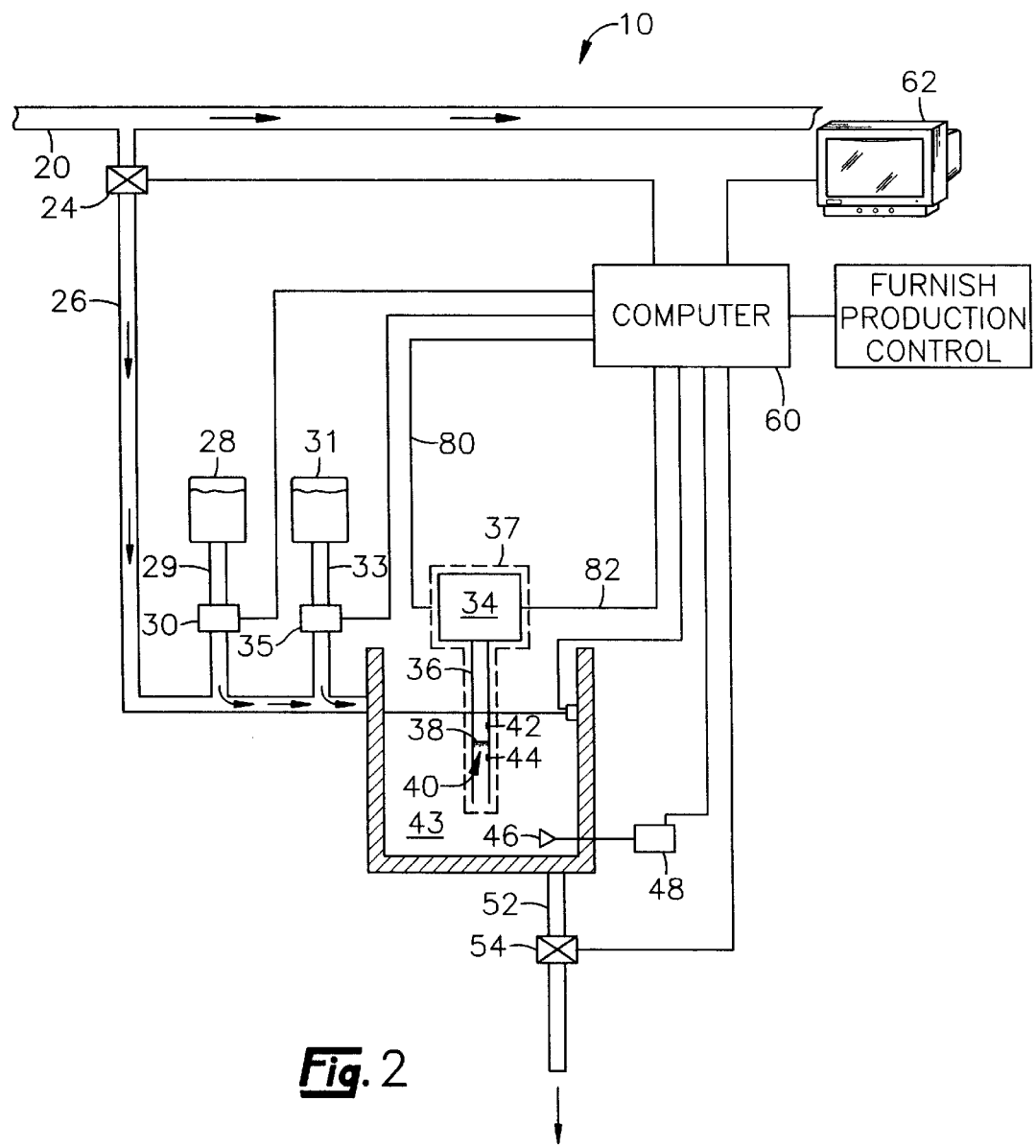
FIG. 2 is a diagrammatical view illustrating features of an apparatus, including a common furnish and titrant supply conduit, for determining the cationic or anionic demand of a papermaking furnish in accordance with a preferred embodiment of the invention.

There are at least two basic procedures for supplying the additive to the furnish. In a preferred procedure shown in FIG. 1, the additive is supplied directly into test chamber 32 through the top of the test chamber 32 and metered with an appropriate measuring device as described above. An alternative procedure is shown in FIG. 2 where the additive is supplied directly to furnish entering test chamber 32 in conduit 26 so that the flow streams merge and are pre-mixed to a degree before entering chamber 32. In one embodiment, the additive is supplied in increments of known amounts (which may or may not be equal) and the streaming potential is measured between each incremental addition, producing a series of streaming potential measurements, until a desired streaming potential value is obtained. The amounts of additive may be plotted against corresponding streaming potential measurements and the resulting curve or mathematical relationship in the form of an equation fitting the curve used to determine the amount of additive needed to achieve a desired streaming potential in the papermaking furnish.

An initial measurement of the sample's streaming potential is preferably taken before the first additive increment. Preferably, several streaming potential measurements are taken and averaged or otherwise statistically analyzed to enhance the reliability of the data. If the initial streaming potential measurement indicates a furnish sample having a cationic colloidal charge, then an anionic material is metered from reservoir 28. If the furnish sample is initially anionic, a cationic material from reservoir 31 will be used. In many cases, the initial charge of the furnish will be known, thereby obviating the need for an initial streaming potential measurement to determine the charge of the additive needed.

Following any initial determination of streaming potential, the additive is supplied in increments and the combination is stirred by a stirrer 46 to allow mixing of fibers and other suspended solids with the additive. In a preferred embodiment, stirrer 46 includes an impeller driven by an electric motor 48 under the control of computer 50. However, other or additional stirring devices may be used instead, including magnetic stirring devices, air sparges, manual stirrers, and the like. Following a set period of stirring, such as five seconds, the streaming potential measurement or measurements are repeated. The measurements and injection of further increments of additive are repeated until the desired streaming potential is reached. For a desired streaming potential of zero, the process is repeated until the sign of the streaming potential device reverses itself. The last two measurements are interpolated to determine the amount of additive corresponding to zero streaming potential. When the desired streaming potential is a nonzero value, additive is injected incrementally until the measured streaming potential value passes the desired value, and the last two measurements are interpolated to determine the amount of additive corresponding to the desired non-zero streaming potential value.

After the desired value is obtained, the ionically modified sample is emptied from the test chamber 32 through a drain line 52 connected at or near the bottom of the test chamber 32. Alternatively, the container contents may be manually emptied. A valve 54, preferably controlled by computer 50, controls the draining of the test chamber 32. After the ionically modified sample is emptied, valve 24 opens to expose the test chamber 32 to a sacrificial aliquot of furnish, which is also emptied from the apparatus before the next measurement cycle.

In accordance with an alternate measurement procedure, the charged additive is added either to the furnish sample line 26 or to the test chamber 32 before the streaming potential measurement is taken. The streaming potential measurement or measurements are taken and the test chamber is emptied and flushed as previously described. Depending on the initial streaming potential value obtained and its variance from the desired final value, the amount of additive is adjusted upwards or downwards before the additive is added and the measurement is repeated with a second furnish sample. The process is repeated until the amount of additive needed to achieve the desired streaming potential value is determined.

According to another alternate measurement procedure shown in FIG. 2, additive is metered continuously to a flow of sample furnish, which preferably is a volumetric (or measured) flow. Streaming potential measurements of the mixed flow are taken and repeated as necessary as the flow of additive is adjusted upwards or downwards until the streaming potential equals the desired value. The amount of additive which was needed to achieve the desired value is then used by papermakers to control the charge of the papermaking furnish. At suitable intervals the flow of furnish sample and charged additive are shut off or diverted so that the test chamber 32 and streaming potential device 37 may be rinsed.

Figure 3:
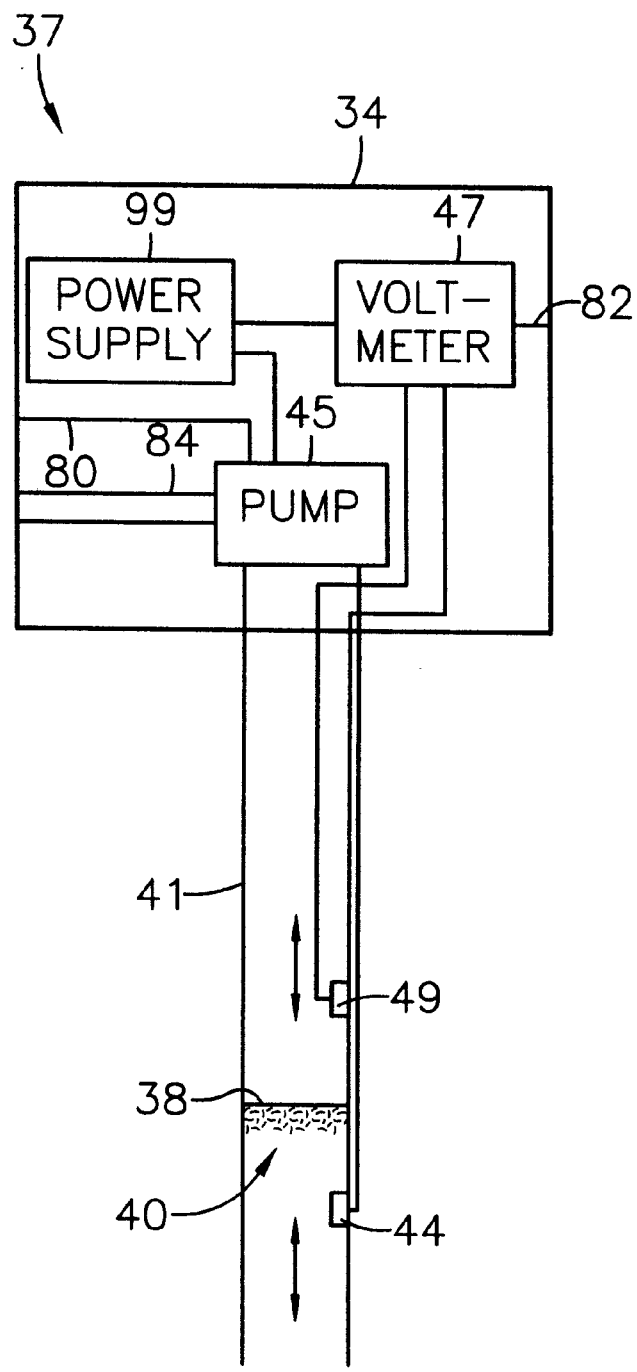
FIG. 3 is a diagrammatic view of a streaming potential measurement device for use with the apparatus illustrated in FIGS. 1 and 2.

With additional reference to FIG. 3, the operation of the streaming potential device 37 will now be described. The streaming potential device 37 in one embodiment includes a standpipe 41 or other suitable conduit having an open bottom which is positioned in the furnish sample and a top which opens to the air space above the furnish sample. A stationary or movable fine mesh screen 38 is positioned within the standpipe 41. In general, the screen 38 may be made of a perforated stainless steel material having perforations in the range of from about 0.1 mm to about 0.5 mm, providing a total fraction of open area in the range of from about 10 percent to 50 percent of the total screen surface area. Alternatively, the screen 38 may be a woven screen of suitable materials such as stainless steel or plastic, having a standard mesh size preferably in the range 20 to 200.

During operation, the pipe 41 is positioned in the fiber slurry sample so that the screen 38 is completely submerged as shown in FIG. 1. A pump 45 positioned within a housing 34 and vented to ambient air by vent 84 is attached to one end of the pipe 41 to create a vacuum which draws the sample furnish up into the pipe 41 and through the screen 38. Computer 60 is programmed to control operation of the pump 45 via line 80. Electrical power for the device 37 is provided by a power supply 99, which may either be a self-contained power supply or one that is dependent on an external source of power.

As the sample furnish flows up through the screen 38, a pad or mat 40 of fibers and other suspended solids is formed on the lower or upstream side of the screen 38. The motion of the fluid through the mat 40 and screen 38 induces a streaming potential which is detected by appropriate connection of a voltmeter 47 to a pair of reversible electrodes 49 and 44. Preferably, one of the electrodes 44 is positioned adjacent the inner surface of the pipe 41 upstream of the pad 40 while the other electrode 49 is positioned adjacent the inner surface downstream of pad 40. Streaming potential is measured and output to the computer 60 via line 82. After the pad 40 is formed and a streaming potential measurement is made by the voltmeter 47, pump 45 reverses and produces positive pressure within the pipe 41 instead of a vacuum. This forces fluid to backflow through the screen 38 to flush out the pad 40 of fibers, which can then be remixed with the furnish sample. To enable the user to verify proper fluid flow through the screen 38 and formation and removal of the fiber pad 40, pipe 41 is preferably transparent.

Although in a preferred embodiment the fiber pad 40 is formed as a result of vacuum pressure applied to the screen 38, it will be understood that the pad 40 may be formed and measurements taken when the screen 38 is subjected to positive pressure. In other words, fluid flow through the screen 38 can be accomplished by either pulling furnish through the screen 38 (vacuum) or pushing furnish through the screen 38 (positive pressure). A preferred pressure difference of from about 0.2 to about 1.0 atmospheres across the screen 38 is used to move furnish through the screen 38, although measurements may be taken over a wider range of pressures, such as from about 0.05 to about 10.0 atmospheres.

The fiber pad 40 may also be formed and removed at the screen 38 by varying the level of the furnish within the test chamber 32 relative to the screen 38, or by moving the screen 38 through pipe 41 with flow out of the pipe 41 in the direction of movement of the screen 38 restricted or deadheaded.

Referring again to the on-line embodiment of FIG. 1, streaming potential measurements output by the voltmeter 47 are received by computer 60 where the measurement results are processed and displayed for user observation on monitor 62. Once the desired streaming potential endpoint is reached, the results are calculated as the amount of titrant used times the concentration of the titrant divided by the volume of furnish that was titrated. This information is used by the papermaker to adjust furnish parameters and composition as needed from future samples. Among these furnish parameters are charged process additives (such as DADMAC, polyamines, and alum) which are introduced to the production furnish to optimize the product and process. The measurements also enable the papermaker (through repeated adjustment of one more process additives to maintain, at: a substantially constant level, the amount of additive or titrant needed to achieve a desired streaming potential in each furnish sample 43) to compensate in a highly effective manner for any changes in the level of dissolved and colloidal anionic materials (disco) in the furnish, or respond to changes in the level of broke, web breaks, and other additive flow changes which otherwise would tend to change the conditions of papermaking. Such compensation may be in the form of changes that the papermaker manually effectuates, or compensation may be fully automated by a computer 60 having control of the furnish production process 64. Because of the rapidity at which furnish composition can change, and because of the complexity of most fiber furnishes, it is preferable to utilize a computer 60 which is programmed and interconnected to control the furnish production system so that it may effect the changes necessary to achieve the desired furnish make-up on an automatic basis.

The following nonlimiting examples further illustrate various aspects of the invention.

EXAMPLE 1

This example demonstrates the use of titrations to determine cationic demand of production dry-lap de-inked pulp. The pulp was obtained at Riverdale Mill in Selma, Ala.

The titrant employed in this example was Bufloc™ 536, a solution of 20 percent poly-diallyldimethylammonium chloride (DADMAC) in water. On a dry basis, pure DADMAC has a cationic colloidal charge density of 6.17 milliequivalent per gram (meq/g). Tests were carried out with a DADMAC titrant solution diluted to 0.1 meq/ml.

Process samples consisted of 50 ml aliquots of 100% de-inked pulp slurry from the pulp vat having an initial solids level or consistency of 4%. The samples were each diluted by a factor of ten using distilled water. Each individual determination of streaming potential involved application of a vacuum to a portion of the furnish sample through a fine-mesh plastic screen.

The screen was a standard double-layer Fourdrinier forming fabric having approximately 40 strands per inch on the side facing the fiber slurry. The open area was approximately 20%. For each test, a pad of fibers was continuously built up on one surface of the screen over a period of 12 seconds at a pressure difference across the pad which increased from zero to about 7.5 psig at the end of the test. A Fluke™ 25 multimeter was used to measure the electrical potential between reversible electrodes located on either side of the fiber pad. The value of the electrical potential (b) measured after the pad had built up was compared with the value (a) obtained at the beginning of each test. The streaming potential was determined by subtracting value (b) from value (a).

Values of cationic demand were obtained by repeated measurements of the streaming potential of the samples following various addition levels of DADMAC titrant solution. The cationic demand was defined as the amount of DADMAC in milliequivalent per liter of undiluted sample required to achieve a streaming potential of zero.

Titrant was added in aliquots of 0.2 to 0.4 milliequivalents per liter of undiluted pulp slurry sample by means of a calibrated syringe. Each such addition was followed by a repeat measurement of the streaming potential. After each measurement of streaming potential, all of the material was returned to its original container to be ready for the next cumulative level of titrant. For example, on the test carried out on day 1 with sample collected at 10 pm, two replicate tests were carried out with successive additions of 0.4, then 0.2, then 0.2 milliequivalents of titrant per liter of sample slurry. In each case the sign of streaming potential was found to have changed between the last two aliquots. For instance, in the first test the second aliquot of titrant resulted in a streaming potential of −2.0 mV, and the third aliquot of titrant resulted in a streaming potential of +0.7 mV. The interpolation was carried out in accordance with the following equation:

$$\text{Colloidal Charge} = 0.6 \text{ meq}/1 + 0.2 \text{ meq}/1 \left( \frac{-2.0 \text{ mV} - 0.0 \text{ mV}}{-2.0 \text{ mV} - 0.7 \text{ mV}} \right) \quad (1)$$

Tests were each conducted within six minutes, and there was no appreciable change in pH during each test.

Results are shown below in Table 1.

TABLE 1

| Day | Time | pH | Cationic Demand |
|---|---|---|---|
| 1 | 10:00 p.m. | 9.64 | 0.73 meq per liter |
| 2 | 4:30 a.m. | 9.70 | 0.74 |
|   | 8:00 a.m. | 9.64 | 0.74 |
|   | 11:00 a.m. | 9.60 | 0.74 |
|   | 12:00 noon | 6.93 | 0.58 |
|   | 1:00 p.m. | 6.35 | 0.66 |
|   | 3:00 p.m. | 6.35 | 0.50 |
|   | 5:00 p.m. | 6.55 | 0.46 |
|   | 6:00 p.m. | 6.10 | 0.49 |
|   | 7:00 p.m. | 6.28 | 0.40 |
|   | 8:00 p.m. | 5.64 | 0.36 |
|   | 9:00 p.m. | 5.79 | 0.40 |
| 4 | 4:00 p.m. | 9.10 | 0.80 |
|   | 5:00 p.m. | 6.54 | 0.40 |
|   | 6:00 p.m. | 6.10 | 0.28 |
|   | 8:00 p.m. | 5.81 | 0.25 |
|   | 9:00 p.m. | 6.53 | 0.29 |

The initial pH level of the furnish varied between a high of 9.64 (day 1, 10:00 p.m.) to a low of 5.64 (day 2, 8:00 p.m.). Although this amount of pH variation is atypical in production furnish, it provided an excellent opportunity to observe the results of the titration process over a wide range of pH levels.

The data shown in Table 1 demonstrates that there is a very strong relationship between the cationic demand and the initial pH level of the furnish. The results are consistent with a greater degree of deprotonation, hence a higher anionic charge, as pH is increased. Thus, the results, which were relatively stable over several days of testing, appear to be highly accurate.

EXAMPLE 2

For this experiment, various pulp samples (as described below in Table 2) were titrated to a zero streaming potential endpoint to determine cationic demand. The test procedures were the same as that described in Example 1. The de-inked pulps described in Table 2 were obtained from a cylinder former during the same production cycles as the samples tested in Example 1. The consistency of the vat was 0.8 to 1.0 percent and the furnish was not diluted for these tests.

The zeta potential was also calculated for each of the samples so that cationic demand determined in accordance with the invention could be compared to zeta potential, which was determined in accordance with the Helmholtz-Smouluchowski equation as given below in equation (2):

$$\zeta = \frac{\Delta E 4\pi\eta\lambda}{\Delta P \epsilon} \quad (2)$$

where:

$\zeta$ is the zeta potential;

$\Delta E$ is the change in measured potential (voltage) in the presence versus absence of a pressure difference across the screen;

$\eta$ is the solution viscosity;

$\lambda$ is the electrical conductivity of the solution;

$\Delta P$ is the pressure applied across the screen during one of the measurements of potential; and $\epsilon$ is the dielectric constant of the solution.

Although equation (2) strictly applies to the case of liquid permeating through cylindrical capillaries, it is well known to those familiar with the art to apply the same equation to the case of a fibrous mat.

The results obtained are shown below in Table 2.

TABLE 2

| Sample Type/Condition Potential | Cationic Demand | Zeta |
|---|---|---|
| De-inked pulp, pH = 9.5 | 290 μeq/l | −6 mV |
| De-inked pulp, pH = 7.0 | 160 | −52 mV |
| De-inked pulp, pH = 7.0 | 100 | −31 mV |
| Bleached hardwood kraft (HW) | 8 | −62 mV |
| HW + $Na_2SO_4$, 687 μS/cm | 16 | −47 mV |
| HW + sodium poly-acrylate | 75 | −108 mV |
| HW + Alknox ™ detergent | 86 | −73 mV |
| HW + Oxidized starch (6%) | 66 | −33 mV |

The data shown in Table 2 demonstrates that there is no generally consistent relationship or proportionality between zeta potential and results achieved by use of the present invention.

EXAMPLE 3

This example highlights a case in which the data obtained by titration, using a streaming potential device incorporating flow through a fiber pad, were completely different from data obtained when the same samples were evaluated in accordance with a prior art titration procedure which uses a streaming current device with a reciprocating motion and PTFE surfaces. The data were obtained from furnish samples of the type used in Example 1 and streaming potential was determined for the samples as described in Example 2.

However, in order to provide a usable sample that would not clog the streaming current apparatus, the samples were squeezed in a potato-ricer to obtain a filtrate in accordance with standard practice. The streaming current of the filtrate was then tested by means of a Chemtrac™ ECA 2000P streaming current detector and titrating with Magnifloc™ 589C, a 20% DADMAC solution very similar to Bufloc™ 536. The results are shown below in Table 3.

TABLE 3

| Day | Time | pH | Invention Results (meq/l) | Streaming Current Results (meq/l) |
|---|---|---|---|---|
| 1 | 9:00 pm | 8.24 | 0.22 | 5.60 |
|   | 10:00 pm | 9.40 | 0.24 | 3.80 |
| 2 | 4:30 am | 9.50 | 0.29 | 2.20 |
|   | 8:00 am | 9.49 | 0.29 | 1.18 |
|   | 11:00 am | 9.46 | 0.26 | 1.63 |
|   | 1:00 pm | 6.93 | 0.16 | 2.96 |
|   | 3:00 pm | 7.00 | 0.10 | 0.67 |
|   | 5:00 pm | 7.96 | 0.13 | 0.96 |
|   | 7:00 pm | 6.65 | 0.14 | 2.08 |
|   | 8:00 pm | 6.68 | 0.10 | 2.73 |
|   | 9:00 pm | 6.76 | 0.08 | 7.70 |
| 4 | 4:00 pm | 8.79 | 0.12 | 0.25 |
|   | 5:00 pm | 7.74 | 0.08 | 1.88 |
|   | 6:00 pm | 6.73 | 0.04 | 12.24 |
|   | 8:00 pm | 6.41 | 0.04 | 13.52 |
|   | 9:00 pm | 6.84 | 0.04 | 10.83 |

From the results shown in Table 3, it can be seen that measuring streaming potential in accordance with the invention produces results which correlate well with the pH of the furnish. For example, when pH is 9.40 (day 1, 10:00), it would not be unreasonable to add titrant in the amount of 0.24 meq/l in order to bring the colloidal charge of the furnish to a zero potential. However, one would not normally need to add titrant in the amount of 3.80 meq/l in order to reach a zero potential of the furnish. The results produced by the invention are consistent and believable, while the results produced by the streaming current method are inconsistent and far removed from what one would normally expect or experience.

EXAMPLE 4

The following example demonstrates that the invention can be used to quantify the amount of anionic colloidal charges in a sample of pulp furnish. To this end, incremental amounts of oxidized starch solution were added to a bleached kraft pulp diluted with distilled water to a consistency of 0.5%. The 100% bleached hardwood kraft had the brand name Astracel™. The pulp was dispersed for 10 minutes with a TAPPI disintegrator at 40° C. The starch solution was prepared from Clinton 441B oxidized starch powder to provide a 0.5% starch solution by mixing the powder with water and heating to 90° C. for 30 minutes in the present of stirring. The following results were obtained by titrating the resultant samples and measuring streaming potential of the titrated samples in accordance with the procedures outlined in Example 1.

TABLE 4

| Sample/Condition | Cationic Demand ($\mu$equiv./liter) |
|---|---|
| Control, pulp only | 8.4 |
| Add 1% starch, dry fiber basis | 18.6 |
| Add 2% starch, dry fiber basis | 28 |
| Add 4% starch, dry fiber basis | 46 |
| Add 6% starch, dry fiber basis | 66 |

Linear regression of the data shown above resulted in an $R^2$ value (coefficient of determination) of 0.9992. The regression intercept was consistent with an inherent cationic demand of 8.6 microequivalents per liter of 0.5% solids hardwood pulp in the absence of the oxidized starch solution. Since the addition of the starch increases the anionic charge of the furnish, these results show a good correlation between the effect starch addition and streaming potential measured according to the invention.

It is contemplated, and will be apparent to those skilled in the art from the foregoing specification, drawings, and examples that numerous modifications and/or changes may be made in the embodiments of the invention. Accordingly, it is expressly intended that the foregoing are only illustrative of preferred embodiments and modes of operation, and that the true spirit and scope of the present invention is to be determined by reference to the appended claims.

What is claimed is:

1. A method for determining electrokinetic properties of a papermaking furnish having a colloidal charge, comprising the steps of:

mixing a sample of the furnish with a measured amount of a cationic or anionic additive to produce an ionically modified furnish;

measuring the streaming potential of the ionically modified furnish sample;

adjusting the amount of additive and mixing the adjusted amount with a furnish sample to provide a second ionically modified furnish sample;

measuring the streaming potential of the second ionically modified furnish sample; and repeating the adjusting, mixing and measuring steps to produce a series of streaming potential measurements corresponding to the adjustments in the amount of additive mixed with the furnish samples.

2. The method of claim 1 wherein the amount of additive in the ionically modified furnish sample is adjusted in uniform increments.

3. The method of claim 1 wherein the amount of additive in the ionically modified furnish sample is adjusted in increments of varying size.

4. The method of claim 1, wherein the step of adjusting the amount of additive and mixing the same with a furnish sample comprises mixing more additive with the same furnish sample used in the previous measurement.

5. A method for determining electrokinetic properties of a papermaking furnish having a colloidal charge, comprising the steps of:

obtaining a series of samples of the furnish in succession;

mixing each of the series of samples with a measured amount of a cationic or anionic additive to produce a series of ionically modified furnish samples, wherein the amount of additive mixed with each further sample of furnish represents an adjustment of the total amount of additive in the ionically modified furnish;

measuring the streaming potential of each ionically modified furnish sample to produce a series of streaming potential measurements corresponding to different amounts of additive in the papermaking furnish sample; and determining from said series of streaming potential measurements an amount of additive which produces a desired colloidal charge in the papermaking furnish.

6. The method of claim 5, further comprising the step of determining from said series of streaming potential measurements an amount of additive which produces a predetermined streaming potential value in the papermaking furnish sample.

7. The method of claim 6, further comprising adjusting at least one charged additive to the papermaking furnish based on said amount of additive needed to achieve a predetermined streaming potential value in the papermaking furnish sample.

8. The method of claim 7, further comprising the step of repeatedly adjusting at least one charged additive to the papermaking furnish so that the amount of additive needed to achieve the predetermined streaming potential is maintained at a substantially constant amount for each of said one or more further samples.

9. The method of claim 5, wherein each adjustment of the amount of additive mixed with a preceding sample of furnish is a uniform, incremental adjustment.

10. The method of claim 5, wherein at least one adjustment of the amount of additive mixed with a preceding sample of furnish varies in the amount of the additive relative to a preceding amount.

11. The method of claim 5, further comprising the step of rinsing the sample chamber with a sacrificial aliquot of furnish after each measurement.

12. A method for determining the amount of a charged additive needed to achieve desired paper formation properties in a papermaking furnish, said method comprising the steps of:

substantially continuously diverting a flow of papermaking furnish from a first flow of papermaking furnish having a first volumetric flow rate to produce a second flow of papermaking furnish having a second volumetric rate less than said first volumetric flow rate;

mixing a charged additive into said second flow of papermaking furnish to produce a flowing stream of ionically modified papermaking furnish; and measuring the streaming potential of said flowing stream of ionically modified papermaking furnish; and adjusting the amount of charged additive mixed in said second flow of papermaking furnish at least once to attain a predetermined streaming potential value of the flowing stream of ionically modified papermaking furnish. substantially constant amount for each of said one or more further samples.

13. The method of claim 12, further comprising repeating the mixing and measuring steps with a different concentration of the same charged additive.

14. The method of claim 12, further comprising repeating the mixing and measuring steps with a different charged additive.

15. The method of claim 12 wherein the amount of additive in the flowing stream of ionically modified papermaking furnish is adjusted in uniform increments.

16. The method of claim 12 wherein the amount of additive in the flowing stream of ionically modified papermaking furnish is adjusted in increments of varying size.

17. The method of claim 12, further comprising measuring the streaming potential of said flowing stream of ionically modified papermaking furnish after each adjustment to produce a series of streaming potential measurements.

18. The method of claim 17, further comprising determining from said series of streaming potential measurements an amount of additive needed to achieve a desired colloidal charge in the papermaking furnish.

19. The method of claim 18, further comprising determining from said series of streaming potential measurements an amount of additive needed to achieve the predetermined streaming potential value in the first flow stream of papermaking furnish.

20. The method of claim 19, further comprising adjusting at least one charged additive to the papermaking furnish based on said amount of additive needed to achieve the predetermined streaming potential value.

21. A method for on-line control of formation qualities of a papermaking furnish having a colloidal charge, said method comprising the steps of:

titrating a sample of papermaking furnish with a charged additive to produce a titrated sample;

measuring the streaming potential of the titrated sample;

further titrating the sample with the charged additive until the streaming potential attains a substantially zero value;

measuring the total amount of charged additive used in attaining the substantially zero value of streaming potential; and adjusting the composition of the papermaking furnish in accordance with said total amount of charged additive to attain a desired colloidal charge in the papermaking furnish.

* * * * *

UNITED STATES PATENT AND TRADEMARK OFFICE
CERTIFICATE OF CORRECTION

PATENT NO. : 6,176,974 B1  Page 1 of 1
DATED : January 23, 2001
INVENTOR(S) : Martin Allen Hubbe It is certified that error appears in the above-identified patent and that said Letters Patent is hereby corrected as shown below:

Column 15, claim 12,
Line 34, after "furnish." delete the phrase "substantially constant amount for each of said one or more further samples."

Signed and Sealed this

Eighteenth Day of December, 2001

Attest:

JAMES E. ROGAN
Attesting Officer   Director of the United States Patent and Trademark Office